(12) United States Patent
Dooley et al.

(10) Patent No.: US 11,712,584 B1
(45) Date of Patent: Aug. 1, 2023

(54) PROSPECTIVE AND RETROSPECTIVE ON-LINE ADAPTIVE RADIOTHERAPY

(71) Applicant: Accuray Incorporated, Sunnyvale, CA (US)

(72) Inventors: John Dooley, Castro Valley, CA (US); Jeremy Heil, Middleton, WI (US); Eric Schnarr, McFarland, WI (US); Richard Holloway, Chapel Hill, NC (US); Charles Brandon Frederick, Raleigh, NC (US); Robert Elijah Broadhurst, Carrboro, NC (US); Kevin Gorczowski, Chapel Hill, NC (US); Jari Toivanen, Redwood City, CA (US); Dylan Casey, Sunnyvale, CA (US); Calvin Maurer, Jr., San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 17/752,625

(22) Filed: May 24, 2022

(51) Int. Cl.
*A61N 5/10* (2006.01)

(52) U.S. Cl.
CPC ............ *A61N 5/1067* (2013.01); *A61N 5/10* (2013.01); *A61N 5/103* (2013.01); *A61N 5/1031* (2013.01);
(Continued)

(58) Field of Classification Search
CPC ........ A61N 5/10; A61N 5/103; A61N 5/1031; A61N 5/1037; A61N 5/1038; A61N 5/1039; A61N 5/1042; A61N 5/1045; A61N 5/1047; A61N 5/1048; A61N 5/1049; A61N 2005/1052; A61N 2005/1054; A61N 2005/1055; A61N 2005/1061; A61N 5/1064; A61N 5/1065; A61N 5/1067;
(Continued)

(56) References Cited

U.S. PATENT DOCUMENTS

| 6,690,965 B1 * | 2/2004 | Riaziat | A61B 6/463 |
| | | | 378/65 |
| 6,914,959 B2 * | 7/2005 | Bailey | A61B 6/482 |
| | | | 378/65 |

(Continued)

OTHER PUBLICATIONS

Carri K. Glide-Hurst et al., Adaptive Radiation Therapy (ART) Strategies and Technical Considerations: A State of the ART Review From NRG Oncology, Int J Radiation Oncol Biol Phys, vol. 109, No. 4, pp. 1054-1075, 2021. (Year: 2021).*

(Continued)

*Primary Examiner* — Allen C. Ho
(74) *Attorney, Agent, or Firm* — Womble Bond Dickinson (US) LLP (57) ABSTRACT

A system and method of performing prospective and retrospective on-line adaptive radiotherapy. The method includes performing, during a treatment delivery session, delivery of a dose of radiation to an anatomical volume. The method includes detecting, during the treatment delivery session, a current state of the anatomical volume. The method includes predicting a future change in the current state of the anatomical volume during the treatment delivery session. The method includes adjusting, while the anatomical volume is in the current state, the treatment delivery to anticipate the future change in the anatomical volume.

28 Claims, 6 Drawing Sheets

(52) U.S. Cl.
CPC ......... *A61N 5/1037* (2013.01); *A61N 5/1038* (2013.01); *A61N 5/1039* (2013.01); *A61N 5/1042* (2013.01); *A61N 5/1045* (2013.01); *A61N 5/1047* (2013.01); *A61N 5/1048* (2013.01); *A61N 5/1049* (2013.01); *A61N 5/1064* (2013.01); *A61N 5/1065* (2013.01); *A61N 5/1068* (2013.01); *A61N 5/1071* (2013.01); *A61N 5/1077* (2013.01); *A61N 5/1081* (2013.01); *A61N 5/1082* (2013.01); *A61N 5/1083* (2013.01); *A61N 2005/1052* (2013.01); *A61N 2005/1054* (2013.01); *A61N 2005/1055* (2013.01); *A61N 2005/1061* (2013.01); *A61N 2005/1072* (2013.01); *A61N 2005/1087* (2013.01)

(58) Field of Classification Search
CPC ............... A61N 5/1068; A61N 5/1071; A61N 2005/1072; A61N 5/1077; A61N 5/1081; A61N 5/1082; A61N 5/1083; A61N 2005/1085; A61N 2005/1087; A61N 2005/1062; A61N 2005/1058; A61N 2005/1059
USPC .......................................... 378/65, 8, 62, 95
See application file for complete search history.

(56) References Cited

U.S. PATENT DOCUMENTS

| | | | | |
|---|---|---|---|---|
| 6,990,175 | B2* | 1/2006 | Nakashima | A61B 6/032 378/92 |
| 7,302,033 | B2* | 11/2007 | Carrano | A61N 5/1049 378/41 |
| 7,469,035 | B2* | 12/2008 | Keall | A61N 5/1042 378/65 |
| 7,564,945 | B2* | 7/2009 | Kim | A61B 6/4447 378/65 |
| 7,570,738 | B2* | 8/2009 | Khamene | A61B 6/032 378/65 |
| 7,609,810 | B2* | 10/2009 | Yi | A61N 5/1049 378/65 |
| 7,623,679 | B2* | 11/2009 | West | G06V 10/255 382/128 |
| 7,672,429 | B2* | 3/2010 | Urano | A61N 5/1049 378/65 |
| 7,894,649 | B2* | 2/2011 | Fu | A61N 5/1049 378/65 |
| 7,907,699 | B2* | 3/2011 | Long | A61N 5/1049 378/65 |
| 8,027,715 | B2* | 9/2011 | Sayeh | A61B 5/113 378/69 |
| 8,042,209 | B2* | 10/2011 | D'Souza | A61N 5/1049 5/610 |
| 8,064,642 | B2* | 11/2011 | Sheng | A61N 5/1049 382/103 |
| 8,073,102 | B2* | 12/2011 | Fallone | A61N 5/103 378/65 |
| 8,073,103 | B2* | 12/2011 | Otto | A61N 5/1042 378/65 |
| 8,121,252 | B2* | 2/2012 | Nord | A61N 5/103 378/65 |
| 8,130,907 | B2* | 3/2012 | Maurer, Jr. | A61B 6/00 378/65 |
| 8,229,068 | B2* | 7/2012 | Lu | A61N 5/1049 378/65 |
| 8,295,435 | B2* | 10/2012 | Wang | G06T 7/33 378/65 |
| 8,306,185 | B2* | 11/2012 | Bal | G16H 20/40 378/65 |
| 8,331,532 | B2* | 12/2012 | Nord | G21K 1/046 378/65 |
| 8,391,955 | B2* | 3/2013 | Erbel | G06T 11/008 600/407 |
| 8,396,270 | B2* | 3/2013 | Keall | A61N 5/1049 382/128 |
| 8,406,844 | B2* | 3/2013 | Ruchala | A61N 5/103 378/65 |
| 8,457,379 | B2* | 6/2013 | Tashiro | A61N 5/1049 382/103 |
| 8,509,383 | B2* | 8/2013 | Lu | A61N 5/1049 378/65 |
| 8,559,596 | B2* | 10/2013 | Thomson | A61B 6/4071 378/65 |
| 8,571,639 | B2* | 10/2013 | Mostafavi | A61B 6/504 600/407 |
| 8,767,917 | B2* | 7/2014 | Ruchala | G16H 50/50 378/65 |
| 8,824,630 | B2* | 9/2014 | Maurer, Jr. | G16H 20/30 378/68 |
| 8,831,706 | B2* | 9/2014 | Fu | A61B 6/037 378/65 |
| 8,837,674 | B2* | 9/2014 | Ruan | A61N 5/1049 378/65 |
| 8,849,633 | B2* | 9/2014 | Core | A61B 6/5264 378/65 |
| 8,861,672 | B2* | 10/2014 | Maltz | A61B 6/5223 378/65 |
| 8,874,187 | B2* | 10/2014 | Thomson | A61B 6/5217 378/65 |
| 8,900,113 | B2* | 12/2014 | Raleigh | A61N 5/1037 600/1 |
| 8,917,813 | B2* | 12/2014 | Maurer, Jr. | A61N 5/1065 378/65 |
| 9,149,654 | B2* | 10/2015 | Handa | A61N 5/1049 |
| 9,248,312 | B2* | 2/2016 | Li | A61N 5/107 |
| 9,271,692 | B2* | 3/2016 | Mostafavi | A61B 8/13 |
| 9,314,160 | B2* | 4/2016 | Adler, Jr. | A61N 5/1064 |
| 9,392,962 | B2* | 7/2016 | Mostafavi | A61B 5/0816 |
| 9,393,443 | B2* | 7/2016 | Fujimoto | A61N 5/1037 |
| 9,433,802 | B2* | 9/2016 | Handa | A61N 5/1049 |
| 9,538,976 | B2* | 1/2017 | Keall | A61B 6/541 |
| 9,616,249 | B2* | 4/2017 | Miyamoto | A61N 5/1049 |
| 9,990,711 | B2* | 6/2018 | Lugosi | G06T 17/10 |
| 10,279,196 | B2* | 5/2019 | West | A61N 5/1031 |
| 10,478,641 | B2* | 11/2019 | Kaneko | A61N 5/1081 |
| 10,500,418 | B2* | 12/2019 | Filiberti | A61N 5/1068 |
| 10,532,224 | B2* | 1/2020 | Jordan | A61N 5/1039 |
| 10,650,585 | B2* | 5/2020 | Kiely | A61B 6/50 |
| 10,835,761 | B2* | 11/2020 | Bériault | A61N 5/1067 |
| 11,040,220 | B2* | 6/2021 | Feain | A61N 5/1039 |
| 11,040,221 | B2* | 6/2021 | Lachaine | G16H 30/20 |
| 11,083,913 | B2* | 8/2021 | Lachaine | A61N 5/1037 |
| 11,090,510 | B2* | 8/2021 | Yan | A61N 5/1067 |
| 11,154,269 | B2* | 10/2021 | Shea | A61B 6/0487 |
| 11,160,537 | B2* | 11/2021 | Bruder | A61N 5/1049 |
| 11,173,324 | B2* | 11/2021 | Paysan | G06T 11/008 |
| 11,410,766 | B2* | 8/2022 | Schreier | G16H 30/40 |
| 11,433,257 | B2* | 9/2022 | Givehchi | A61N 5/1049 |
| 11,446,520 | B2* | 9/2022 | Fujii | A61N 5/1048 |
| 11,504,550 | B2* | 11/2022 | Maolinbay | A61N 5/1067 |

OTHER PUBLICATIONS

Stephanie Lim-Reinders et al., Online Adaptive Radiation Therapy, Int J Radiation Oncol Biol Phys, vol. 99, No. 4, pp. 994-1003, 2017. (Year: 2017).*

* cited by examiner

PROSPECTIVE AND RETROSPECTIVE ON-LINE ADAPTIVE RADIOTHERAPY

TECHNICAL FIELD

The present disclosure relates generally to radiation treatment, and more particularly, to systems and methods of performing prospective and retrospective on-line adaptive radiotherapy.

BACKGROUND

In radiation treatment, a radiation delivery system may utilize a therapeutic radiation source to generate a treatment beam that provides a therapeutic dose of radiation to a target, such as a tumor of a patient. The radiation source may also operate in a mode that delivers a diagnostic imaging beam for the purposes of patient tumor imaging.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

A conventional radiation delivery system generates a treatment beam (e.g., a megavolt (MV) treatment beam) using a therapeutic radiation source to provide a therapeutic dose of radiation to a target, such as a tumor of a patient. During the radiation therapy treatment delivery, the goal is to deliver, as closely as possible, the planned dose. However, multiple factors can cause deviations between the planned and delivered dose. These factors may include, for example, gross patient movement, discrete physiological movements that cause internal deformation of the patient, or periodic patient movements, such as respiration or deviations from modeled respiration.

To compensate for these dose deviations, a conventional radiation therapy treatment delivery system may adjust the currently delivered beam according to several techniques in order to increase or decrease the delivered dose with respect to the planned dose. For example, a conventional radiation therapy treatment delivery system may adjust the pointing vector of the beam to compensate for the gross motions. As another example, a conventional radiation therapy treatment delivery system may compensate for the motion of the patient by gating or interrupting the beam. As another example, a radiation therapy treatment delivery system can detect the motion of the patient using implanted sensors and disable the beam if the target position deviates too far from the beam axis. Thus, a conventional radiation therapy treatment delivery system that implements any of these beam adjustment techniques can effectively control the delivery of a dose of radiation.

The problem, however, is that the conventional radiation treatment delivery system cannot determine, during treatment (e.g., in real time), the precise moment in which the dose of radiation should be deviated from the planned dose. Consequently, the conventional radiation therapy treatment system is incapable of using the beam adjustment techniques to compensate for the dose deviations that occur during treatment, which in turn, causes the conventional radiation treatment delivery system to deliver the wrong dose of radiation to the patient.

Aspects of the present disclosure address the above-noted and other deficiencies by performing prospective and retrospective on-line adaptive radiotherapy to improve the agreement between delivered and planned doses of radiation. Prior to beginning a treatment delivery session, a prospective and retrospective on-line adaptive radiotherapy (PRO-ART) system generates a treatment plan for a planned dose of radiation for a patient based on a patient model, a motion model, and/or a deformation model of the patient. The PRO-ART system performs delivery of a radiation dose to an anatomical volume of the patient according to the treatment plan. During the treatment delivery session, the PRO-ART system detects a current state (e.g., movement, positioning, etc.) of the anatomical volume of the patient. The PRO-ART system predicts, based on the detected current state, a future change in the current state of the anatomical volume that will likely take place during the treatment delivery session. The PRO-ART system adjusts, while the anatomical volume is in the current state, the treatment delivery to anticipate the future change in the anatomical volume by compensating for the resultant dose deviation.

The compensation can occur either before or after an undesirable patient position is detected or calculated. That is, if the dose compensation anticipates a predicted future difference, it is called prospective adaptive therapy. If the dose compensation occurs after the planned dose is reduced, it is called retrospective adaptive therapy.

The PRO-ART system uses the detected and predicted dose differences that are due to the changing patient anatomy to adapt the plan so that the radiation delivery more closely matches the plan. This adaptation may involve delivering more or less dose in the current configuration or for an anticipated future machine configuration. The change in dose may compensate for anticipated favorable or problematic configurations later in the treatment or unplanned problems with or opportunities for the current configuration of the PRO-ART system.

Adaptation of the delivery may be enabled by slowing down, stopping, or reversing the motion of the treatment couch. It may also include adjustment of multileaf collimator (MLC) leaves and/or a jaw position. These adjustments are especially useful for transient patient positions because they allow multiple shots from the same position.

The PRO-ART system may interleave projections in order to get multiple passes at the anatomical volume. In this embodiment, the PRO-ART system may determine (during treatment) the pass in which the patient configuration is closest to the planned patient configuration. The interleaved projection spacing can be optimized to improve the probability of getting good beam deliveries relative to the anatomical volume.

Thus, by predicting a future change in the current state of the anatomical volume, the PRO-ART system is able to determine, during treatment, the precise moment in which the dose of radiation should be deviated from the planned dose. This allows the PRO-ART system to optimize the delivery of radiation to a patient by using beam adjustment techniques that compensate for dose deviations. The conventional radiation treatment delivery system lacks these advantages.

Figure 1:
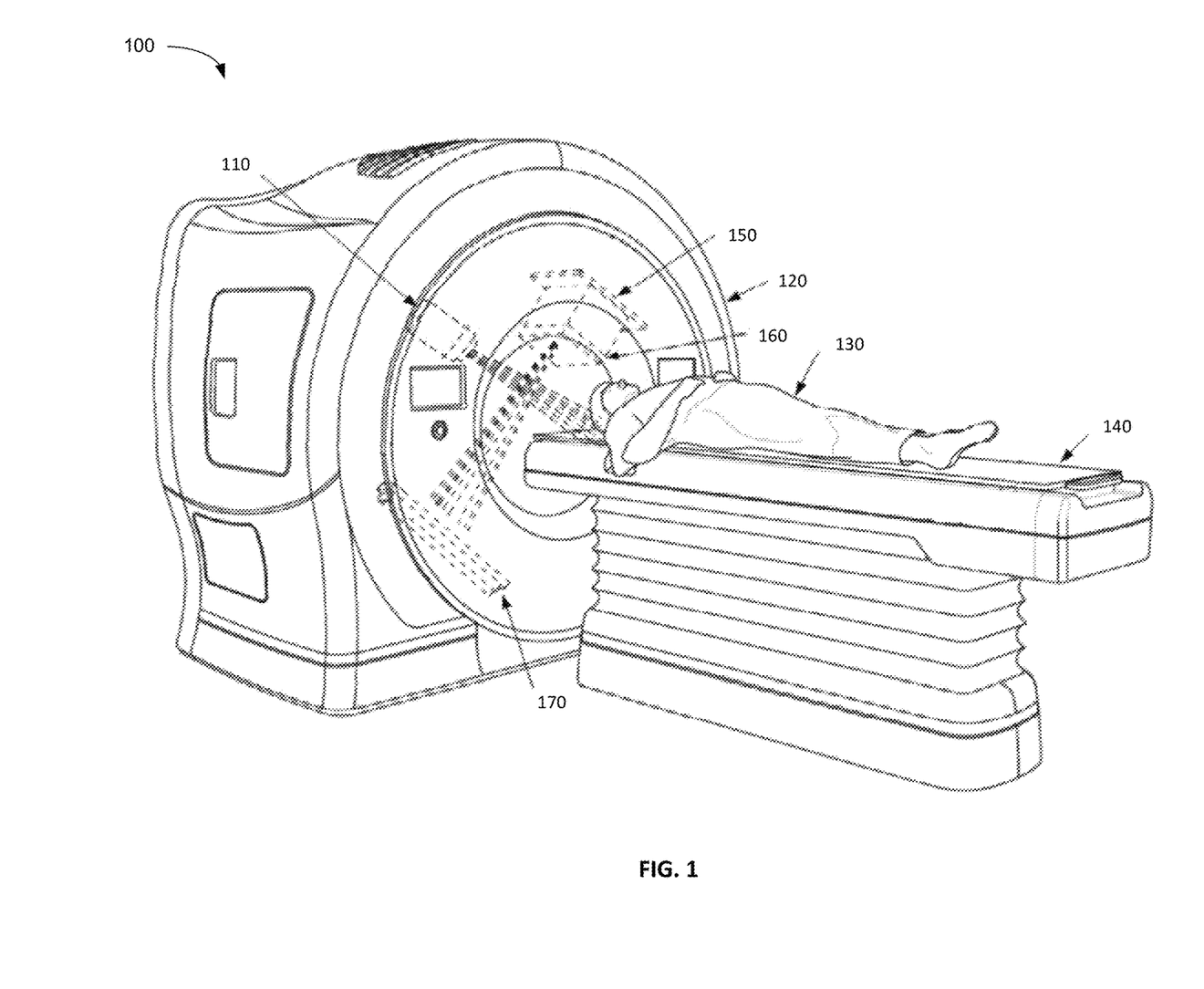
FIG. 1 illustrates a helical radiation delivery system, according to some embodiments.

FIG. 1 illustrates a helical radiation delivery system 100, according to some embodiments. The helical radiation delivery system 100 may include a linear accelerator (LINAC) 150 mounted to a ring gantry 120. The LINAC 150 may be used to generate a radiation beam (i.e., treatment beam) by directing an electron beam towards an x-ray emitting target.

In some embodiments, the "anatomical volume" of a patient includes a target (sometimes referred to as, "target region") and anatomical tissue (sometimes referred to as, "critical structure") of the patient that surrounds the target. In some embodiments, the "target" of a patient is a region of the patient that the radiation delivery system intends to treat with radiation. For example, the target of the patient may be one or more of the following: a tumor, a lesion, a metastatic mass, and/or a nodule. The target may also include a margin about the tumor to account for microscopic disease and delivery uncertainties. The target may also include one or more features that are indicative of other non-tumor clinical conditions.

The treatment beam of the LINAC 150 may deliver radiation to a target region of a patient or an anatomical volume of the patient. The treatment helical radiation delivery system 100 further includes a multileaf collimator (MLC) 160 coupled with the distal end of the LINAC 150. The MLC 160 includes a housing that houses multiple leaves that are movable to adjust an aperture of the MLC 160 to enable shaping of the treatment beam. In some embodiments, the MLC 160 may be a binary MLC that includes a plurality of leaves arranged in two opposing banks, where the leaves of the two opposing banks are interdigitated with one another and can be opened or closed to form an aperture. In some embodiments, the MLC 160 may be an electromagnetically-actuated MLC. In some embodiments, MLC 160 may be any other type of MLC. The ring gantry 120 has a toroidal shape in which the patient 130 extends through a bore of the ring/toroid and the LINAC 150 is mounted on the perimeter of the ring and rotates about the axis passing through the center to irradiate a target region with beams delivered from one or more angles around the patient. During treatment, the patient 130 may be simultaneously moved through the bore of the gantry on a treatment couch 140.

The helical radiation delivery system 100 includes an imaging system, comprising the LINAC 150 as an imaging source and an x-ray detector 170. The LINAC 150 may be used to generate a mega-voltage x-ray image (MVCT) of a region of interest (ROI) of patient 130 by directing a sequence of x-ray beams at the ROI which are incident on the x-ray detector 170 opposite the LINAC 150 to image the patient 130 for setup and generate pre-treatment images. In one embodiment, the helical radiation delivery system 100 may also include a secondary imaging system consisting of a kV imaging source 110 mounted orthogonally relative to the LINAC 150 (e.g., separated by 90 degrees) on the ring gantry 120 and may be aligned to project an imaging x-ray beam at a target region and to illuminate an imaging plane of a detector after passing through the patient 130.

Figure 2:
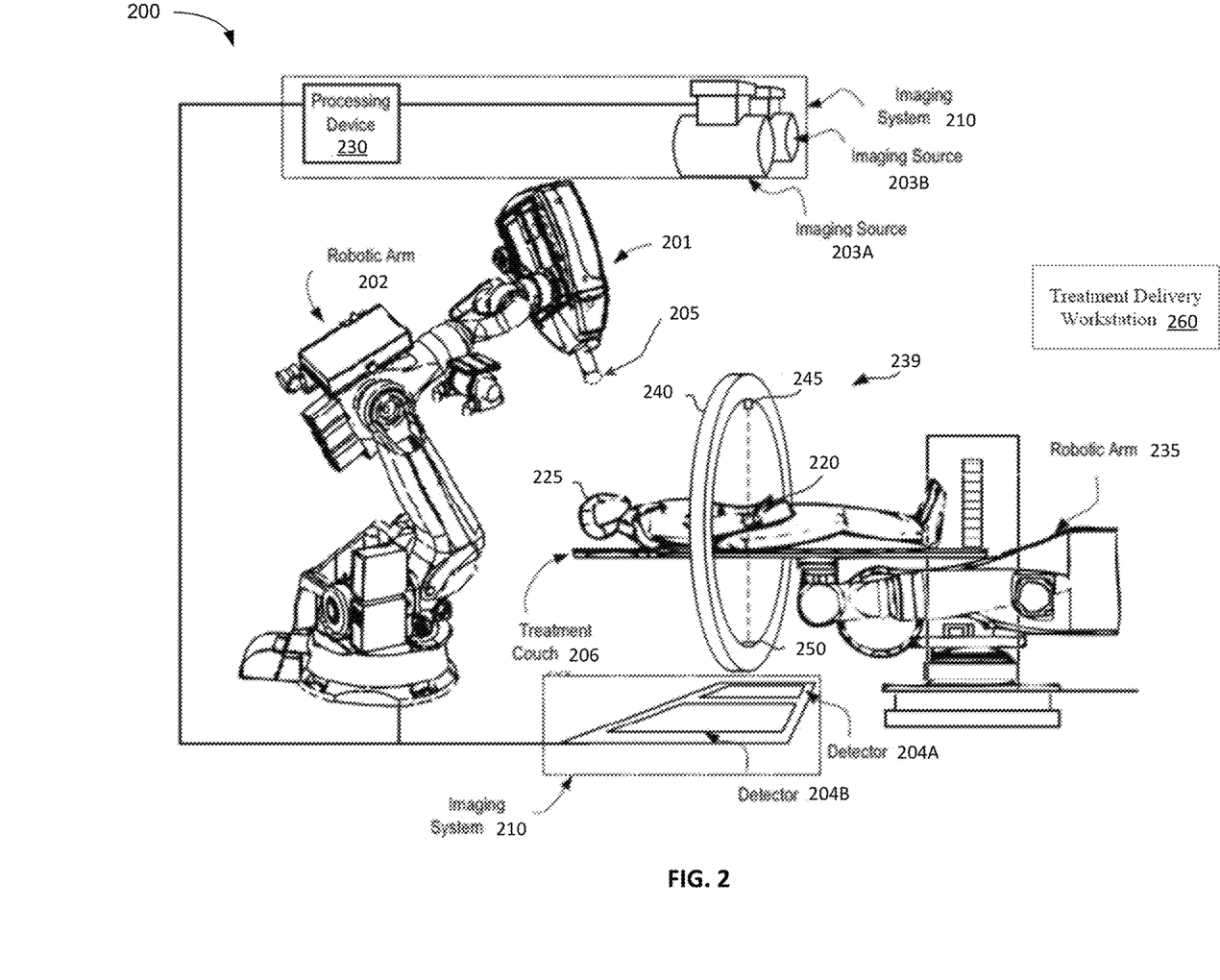
FIG. 2 illustrates a robotic radiation treatment system, according to some embodiments.

FIG. 2 illustrates a robotic radiation treatment system 200, according to some embodiments. As shown, FIG. 2 illustrates a configuration of a radiation treatment system 200. In the illustrated embodiments, the radiation treatment system 200 includes a linear accelerator (LINAC) 201 that acts as a radiation treatment source and an MLC 205 coupled with the distal end of the LINAC 201 to shape the treatment beam. In one embodiment, the LINAC 201 is mounted on the end of a robotic arm 202 having multiple (e.g., 5 or more) degrees of freedom in order to position the LINAC 201 to irradiate a pathological anatomy (e.g., target) with beams delivered from many angles, in many planes, in an operating volume around a patient. Treatment may involve beam paths with a single isocenter, multiple isocenters, or with a non-isocentric approach.

The LINAC 201 may be positioned at multiple different nodes (predefined positions at which the LINAC 201 is stopped and radiation may be delivered) during treatment by moving the robotic arm 202. At the nodes, the LINAC 201 can deliver one or more radiation treatment beams to a target, where the radiation beam shape is determined by the leaf positions in the MLC 205. The nodes may be arranged in an approximately spherical distribution about a patient. The particular number of nodes and the number of treatment beams applied at each node may vary as a function of the location and type of pathological anatomy to be treated.

In another embodiment, the robotic arm 202 and LINAC 201 at its end may be in continuous motion between nodes while radiation is being delivered. The radiation beam shape and 2-D intensity map is determined by rapid motion of the leaves in the MLC 205 during the continuous motion of the LINAC 201.

In some embodiments, the radiation treatment system 200 may include an imaging system 210 having a processing device 230 connected with x-ray sources 203A and 203B (i.e., imaging sources) and fixed x-ray detectors 204A and 204B. The imaging system 210 may be utilized to generate additional imaging beams. Alternatively, the x-ray sources 203A, 203B and/or x-ray detectors 204A, 204B may be mobile, in which case they may be repositioned to maintain alignment with the target, or alternatively to image the target from different orientations or to acquire many x-ray images and reconstruct a three-dimensional (3D) cone-beam CT. In one embodiment, LINAC 201 serves as an imaging source, where the power level of the LINAC 201 is reduced to acceptable levels for imaging.

The imaging system 210 may perform computed tomography (CT) such as cone beam CT or helical megavoltage computed tomography (MVCT), and images generated by imaging system 210 may be two-dimensional (2D) or three-dimensional (3D). The two x-ray sources 203A and 203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 206 during treatment) and to illuminate imaging planes of respective detectors 204A and 204B after passing through the patient. In one embodiment, imaging system 210 provides stereoscopic imaging of a target and the surrounding volume of interest (VOI). In other embodiments, imaging system 210 may include more or less than two x-ray sources and more or less than two detectors, and any of the detectors may be movable rather than fixed. In yet other embodiments, the positions of the x-ray sources and the detectors may be interchanged. Detectors 204A and 204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In one embodiment, IGRT delivery system 200 also includes a secondary imaging system 239. Imaging system 239 may be a Cone Beam Computed Tomography (CBCT) imaging system. Alternatively, other types of volumetric imaging systems may be used. The secondary imaging system 239 includes a rotatable gantry 240 (e.g., a ring) attached to an arm and rail system (not shown) that move the rotatable gantry 240 along one or more axes (e.g., along an axis that extends from a head to a foot of the treatment couch 206. An imaging source 245 and a detector 250 are mounted to the rotatable gantry 240. The rotatable gantry 240 may rotate 360 degrees about the axis that extends from the head to the foot of the treatment couch. Accordingly, the imaging source 245 and detector 250 may be positioned at numerous different angles. In one embodiment, the imaging source 245 is an x-ray source and the detector 250 is an x-ray detector. In one embodiment, the secondary imaging system 239 includes two rings that are separately rotatable. The imaging source 245 may be mounted to a first ring and the detector 250 may be mounted to a second ring. In one embodiment, the rotatable gantry 240 rests at a foot of the treatment couch during radiation treatment delivery to avoid collisions with the robotic arm 202.

As shown in FIG. 2, the image-guided radiation treatment system 200 may further be associated with a treatment delivery workstation 260. The treatment delivery workstation 260 may be remotely located from the radiation treatment system 200 in a different room than the treatment room in which the radiation treatment system 200 and patient are located. The treatment delivery workstation 260 may include a processing device (which may be processing device 230 or another processing device) and memory that modify a treatment delivery to the patient 225 based on a detection of a target motion that is based on one or more image registrations, as described herein.

Figure 3:
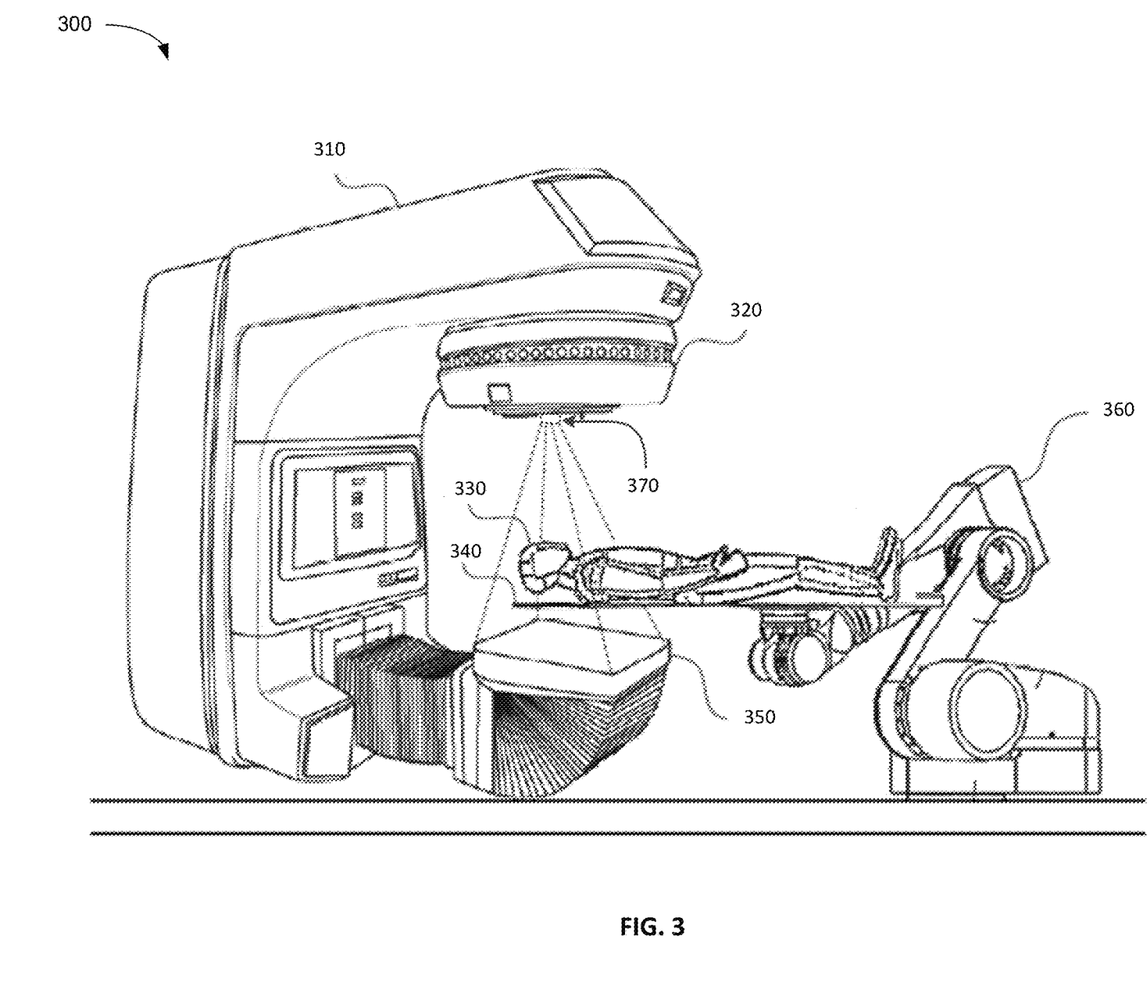
FIG. 3 illustrates a C-arm gantry-based radiation treatment system, according to some embodiments.

FIG. 3 illustrates a C-arm gantry-based radiation treatment system 300, according to some embodiments. In one embodiment, in the C-arm gantry-based radiation treatment system 300 the beam energy of a LINAC may be adjusted during treatment and may allow the LINAC to be used for both x-ray imaging and radiation treatment. In another embodiment, the C-arm gantry-based radiation treatment system 300 may include an onboard kV imaging system to generate x-ray images and a separate LINAC to generate the higher energy therapeutic radiation beams. The C-arm gantry-based radiation treatment system 300 includes a C-arm gantry 310, a LINAC 320, an MLC 370 coupled with the distal end of the LINAC 320 to shape the beam, and a portal imaging detector 350. The C-arm gantry 310 may be rotated to an angle corresponding to a selected projection and used to acquire an x-ray image of a VOI of a patient 330 on a treatment couch 340. In embodiments that include a portal imaging system, the LINAC 320 may generate an x-ray beam that passes through the target of the patient 330 and are incident on the portal imaging detector 350, creating an x-ray image of the target. After the x-ray image of the target has been generated, the beam energy of the LINAC 320 may be increased so the LINAC 320 may generate a radiation beam to treat a target region of the patient 330. In another embodiment, the kV imaging system may generate an x-ray beam that passes through the target of the patient 330, creating an x-ray image of the target. In some embodiments, the portal imaging system may acquire portal images during the delivery of a treatment. The portal imaging detector 350 may measure the exit radiation fluence after the beam passes through the patient 330. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 4:
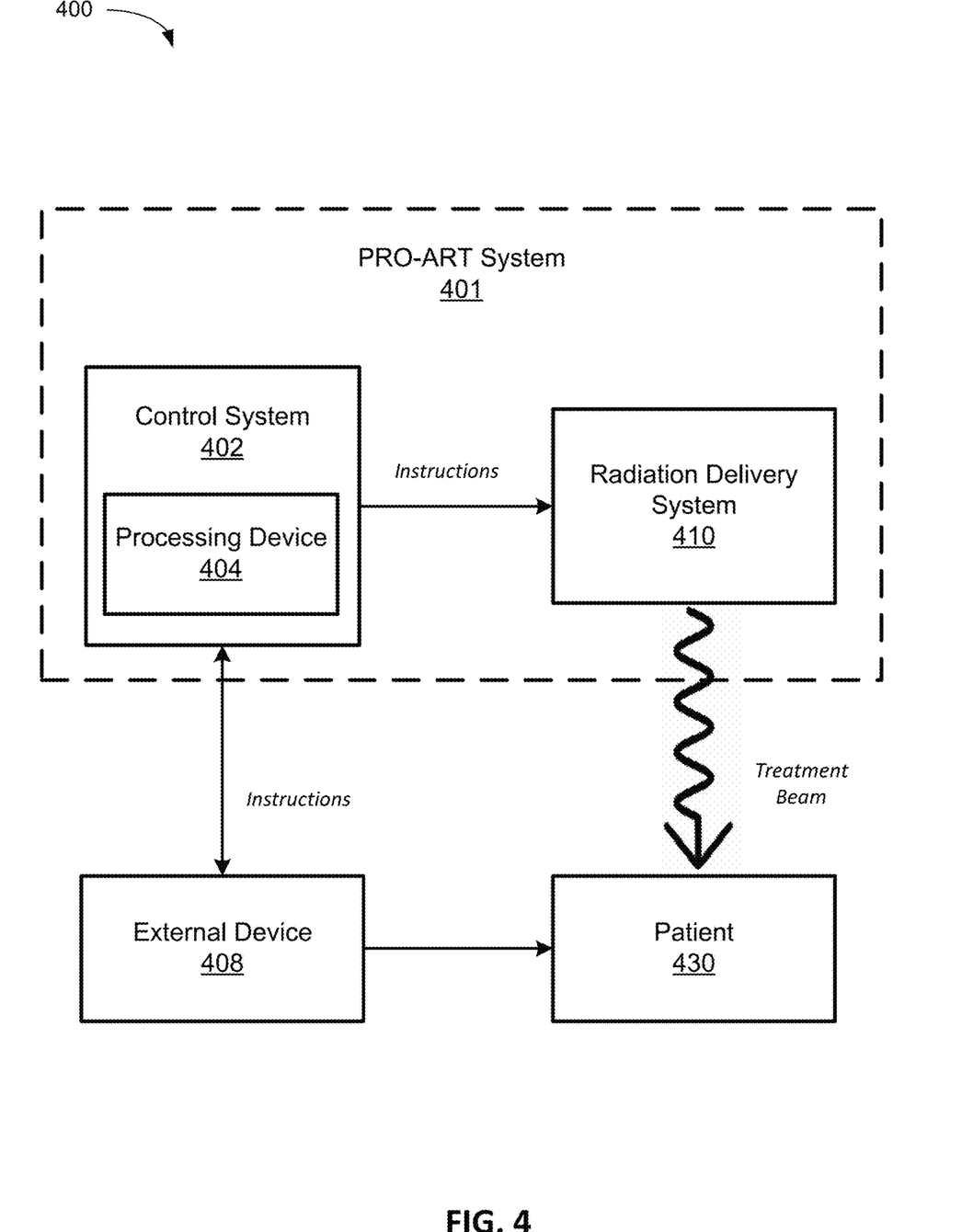
FIG. 4 is a block diagram depicting an example environment for performing prospective and retrospective on-line adaptive radiotherapy, according to some embodiments.

FIG. 4 is a block diagram depicting an example environment for performing prospective and retrospective on-line adaptive radiotherapy, according to some embodiments. The environment 400 includes a prospective and retrospective on-line adaptive radiotherapy (PRO-ART) system 401 and an external device 408. The PRO-ART system 401 includes a control system 402 and a radiation delivery system 410 that are each operatively coupled to the external device 408 via one or more communication links (e.g., wired or wireless).

The radiation delivery system 410 is configured to receive instructions (e.g., commands) from the control system 402 via the one or more communication links. The instructions cause the radiation delivery system 410 to utilize a therapeutic radiation source to generate a treatment beam. The treatment beam provides a therapeutic dose of radiation to a target (or target region) or anatomical volume of the patient 430. In some embodiments, the radiation delivery system 410 may correspond to, and include one or more components of the helical radiation delivery system 100 in FIG. 1. In some embodiments, the radiation delivery system 410 may correspond to, and include one or more components of the radiation treatment system 200 in FIG. 2. In some embodiments, the radiation delivery system 410 may correspond to, and include one or more components of the C-arm gantry-based radiation treatment system 300 in FIG. 3.

The external device 408 may be a ventilator that is configured to control the respiration of the patient 430. The external device 408 may be an imaging device that is configured to take images of the patient 430. The external device 408 may be an applicator that is configured to control a flow rate of a contrast agent for an image (e.g., X-ray, CT, etc.). In some embodiments, the radiation delivery system 410 may include the external device 408.

The control system 402 may include a processing device 404 that includes processing logic that controls the radiation delivery system 410. In some embodiments, the control system 402 controls the radiation delivery system 410 by sending instructions (e.g., commands) to the radiation delivery system 410, which cause the radiation delivery system to execute the instructions. In some embodiments, processing device 404 may be provided by one or more general-purpose processing devices such as a microprocessor, central processing unit, or the like. In an illustrative example, processing device 404 may include a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 404 may also comprise one or more special-purpose processing devices such as an application specific integrated circuit (ASIC), a field programmable gate array (FPGA), a digital signal processor (DSP), network processor, or the like.

The PRO-ART system 401 may generate a patient model for the patient 430. The patient model may include information indicative of anatomic structures (e.g., shape, size, volume, surface area, height, weight) of the patient 430 and demographics (e.g., age, gender) of the patient 430. The patient model may include a motion model that anticipates the voluntary movements (e.g., moving arms and legs) and/or the involuntary (e.g., breathing) movements of the patient 430 that will likely occur during a treatment delivery session. The patient model may include a deformation model which is indicative of deformation model which can map limited information (such as 2D images) to likely anatomical changes in patient anatomy; this gives a statistically probable estimate of the patient's 3D geometry with limited information at time of treatment. Such deformation models are further discussed in International Pat. App. No. PCT/US2020/061112, entitled "PARTIAL DEFORMATION MAPS FOR RECONSTRUCTING MOTION-AFFECTED TREATMENT DOSE USING MACHINE LEARNING," which is herein incorporated by reference in its entirety.

The PRO-ART system 401 may generate a treatment plan for a planned dose of radiation for the patient 430. The PRO-ART system 401 may generate a treatment plan based on the patient model, the motion model, and/or the deformation model of the patient 430. In some embodiments, the PRO-ART system 401 may generate the treatment plan prior to beginning a treatment delivery session for the patient 430.

The PRO-ART system 401 may perform, during a treatment delivery session, a delivery of a radiation dose to an anatomical volume of the patient 430. The PRO-ART system 401 may deliver the radiation dose to the anatomical volume of the patient 430 based on a treatment plan that is indicative of a planned dose of radiation. In some embodiments, the PRO-ART system 401 may perform the delivery of the radiation dose to the anatomical volume by generating the treatment beam for proton therapy.

The PRO-ART system 401 may detect, during the treatment delivery session, a current state (e.g., position, shape, breathing rate, etc.) of the anatomical volume. In some embodiments, the PRO-ART system 401 may use imaging equipment and/or a motion detector of the radiation delivery system 410 or the external device 408 to detect that the patient 430 is currently moving during the treatment delivery session. In some embodiments, the PRO-ART system 401 may use a heart rate monitor (e.g., electrocardiogram (EKG)) of the radiation delivery system 410 or the external device 408 to detect that the patient 430 is currently moving during the treatment delivery session. In some embodiments, the PRO-ART system 401 may use an oxygen saturation monitor (e.g., SpO2) of the radiation delivery system 410 or the external device 408 to detect that the patient 430 is currently moving during the treatment delivery session.

The control system 402 may use respiratory equipment of the radiation delivery system 410 or the external device 408 to detect the current breathing rate of the patient 430 and use the current breathing rate to determine that the patient is currently moving. For example, the PRO-ART system 401 may use respiratory equipment to detect that the patient's 430 breaths are shallower, faster, or slower than anticipated according to a motion model of an imaging scan (e.g., 4D CT scan) that was used to generate the treatment plan for the patient 430. The PRO-ART system 401 may detect the current state of the anatomical volume based on one or more respiratory traces and/or images of the anatomical volume. In some embodiments, the images may include one or more computed tomography (CT) images, an X-ray images, positron emission tomography (PET) images, magnetic resonance imaging (MRI) images, ultrasound images, and/or single photon emission computed tomography (SPECT) images.

The PRO-ART system 401 may predict a future change in the current state of the anatomical volume (e.g., the target and the surrounding anatomical tissue) during the treatment delivery session. In some embodiments, the control system 402 may predict a future change in the current state of the target only, without considering any possible change in the surrounding anatomical tissue. The PRO-ART system 401 may predict a future change in the current state of the anatomical volume during the treatment delivery session based on images, respiratory traces, breathing rate, motion detector information, and/or oxygen saturation (SpO2) information of the patient 430.

The PRO-ART system 401 may determine, during the treatment delivery session, that the future change in the current state of the anatomical volume is an unexpected change. That is, a treatment plan for a patient 430 may indicate that the patient 430 is likely to undergo certain types of movements during the treatment delivery session. In contrast, the unexpected change refers to any movements of the patient 430 that were not accounted for in the treatment plan (which was generated prior to the treatment delivery session).

The PRO-ART system 401 may determine that the future change in the current state of the anatomical volume will cause a dose difference between the dose of radiation that is delivered to the anatomical volume and the planned dose of radiation (as indicated in the treatment plan). The PRO-ART system 401 may determine that the future change in the current state of the anatomical volume will cause one or more imaging times used for motion tracking of the anatomical volume to be aliased on a breathing phase. In response, the PRO-ART system 401 may capture, while the anatomical volume is in the current state, an image at a different breathing phase. The PRO-ART system 401 may determine that the future change in the current state of the anatomical volume is caused by a respiratory motion of the anatomical volume.

The PRO-ART system 401 may adjust (e.g., modify, regulate), while the anatomical volume is in the current state, the treatment delivery to anticipate the future change in the anatomical volume. The PRO-ART system 401 may adjust the treatment delivery by adjusting the treatment beam (e.g., beam strength, beam angle, beam shape, beam orientation, etc.) and/or the imaging parameters (e.g., exposure time, current, beam energy, aperture, imaging frequency, etc.).

The PRO-ART system 401 may adjust the treatment beam in response to determining that the future change in the current state of the anatomical volume is caused by a respiratory motion of the anatomical volume. The PRO-ART system 401 may adjust the treatment beam to increase the dose of radiation to the anatomical volume while the anatomical volume is in the current state. The PRO-ART system 401 may adjust the treatment beam to decrease the dose of radiation to the anatomical volume while the anatomical volume is in a future configuration corresponding to the future change in the current state of the anatomical volume.

The PRO-ART system 401 may predict, while the anatomical volume is in the current state, that a future state of the anatomical volume will cause a degradation of an ability of the PRO-ART system 401 to track a motion of the anatomical volume. In response, the PRO-ART system 401 may adjust, while the anatomical volume is in the current state, one or more imaging control parameters of the external device 408 to mitigate the degradation of the ability to track motion in the future state. For example, the external device 408 may be a ventilator, such that the PRO-ART system 401 may control the respiration to control the breathing rate of the patient 430. As another example, the external device 408 may be an applicator, such that the PRO-ART system 401 may control the applicator to control a flow rate of a contrast agent for an image. As another example, the external device 408 may be an imaging device, such that the PRO-ART system 401 may control the imaging device to control an imaging time (e.g., time when an image is taken), image energy (e.g., photon count), an imaging location, an imaging angle, an exposure time of the treatment beam, a timing of the treatment beam, an imaging frequency, and/or an imaging modality (e.g., single-energy image or dual-energy image).

The PRO-ART system 401 may determine that the future change in the current state of the anatomical volume is caused by a deformation that affects at least one of a relative position of the anatomical volume. In some embodiments, the deformation of the anatomical volume is unrelated to a respiratory motion of the anatomical volume. In response, the PRO-ART system 401 may adjust the treatment beam to increase the dose of radiation to the anatomical volume when the beam does not intersect the anatomical structure. In response, the PRO-ART system 401 may adjust the treatment beam to decrease the dose of radiation to the anatomical volume when the beam intersects the anatomical structure.

The PRO-ART system 401 may generate the treatment beam using the LINAC 150 in FIG. 1. The PRO-ART system 401 may determine that the future change in the current state of the anatomical volume causes an absence of the anatomical volume from a field of view of the treatment beam during a rotation of the LINAC 150 around the anatomical volume. In response, the PRO-ART system 401 may adjust the treatment beam to prevent the dose of radiation to the anatomical volume during the rotation of the LINAC 150 around the anatomical volume, and/or adjust the treatment beam to increase the dose of radiation to the anatomical volume during a different rotation of the LINAC 150 around the anatomical volume. In some embodiments, the anatomical volume is continuously within the field of view of the treatment beam during the different rotation of the LINAC 150 around the anatomical volume.

The PRO-ART system 401 may determine a position of the anatomical volume during the rotation of the LINAC 150 around the anatomical volume to generate a determined position. The PRO-ART system 401 may determine a confidence score associated with the determined position of the anatomical volume. The PRO-ART system 401 may determine the absence of the anatomical volume from the field of view of the treatment beam based on the confidence score.

The PRO-ART system 401 may adjust the treatment beam to compensate for the dose difference caused by the future change in the current state of the anatomical volume by adjusting one or more control parameters of a collimator, adjusting a motion of a treatment couch, adjusting one or more leaves of a multileaf collimator (MLC) (e.g., MLC 160 in FIG. 1), adjusting a jaw position, adjusting a position of a robot (e.g., robotic arm 235 in FIG. 2), adjusting a position of a gantry (e.g., ring gantry 120 in FIG. 1), and/or adjusting a position of a couch (e.g., treatment couch 206 in FIG. 2).

In some embodiments (sometimes referred to as, "respiratory compensation"), the PRO-ART system 401 may detect, during treatment, that the patient's 430 breaths are shallower, faster, or slower than anticipated according to a motion model of an imaging scan (e.g., 4D CT scan) that was used to generate the treatment plan for the patient 430. The respiratory change may increase the time a critical structure occludes the target. The PRO-ART system 401 may anticipate this change by reducing the dose delivered, and increasing the dose delivered to an earlier or later configuration that has an unobstructed view of the to the anatomical volume.

In some embodiments (sometimes referred to as, "non-respiratory compensation"), the PRO-ART system 401 may detect, during treatment based on an image, an anatomical deformation that affects the relative position of a critical structure and a target volume. In this embodiment, the treatment plan would deliver more dose to the critical structure than planned. Therefore, the PRO-ART system 401 adapts (e.g., updates) the treatment plan to deliver less dose from the impacted configuration and compensate for the under dose by delivering more dose from configurations that do not have a beam intersection with the critical structure.

In some embodiments, the PRO-ART system 401 may determine that the patient configuration has changed since the generation of the treatment plan, and the anatomical volume is not in the field of view of the delivery beam at a delivery configuration. For example, the treatment plan may call for a dose delivery during one rotation of a LINAC, but the anatomical volume is no longer in view or is only partially in view during that rotation. The PRO-ART system 401 may compensate by delivering no dose during this rotation and deliver additional dose in a different rotation.

In some embodiments, the PRO-ART system 401 may infer a tumor position where the confidence in the position of the anatomical volume is low during a specific rotation. The PRO-ART system 401 may compensate by delivering no dose during this rotation and deliver additional dose in a different rotation.

Figure 5:
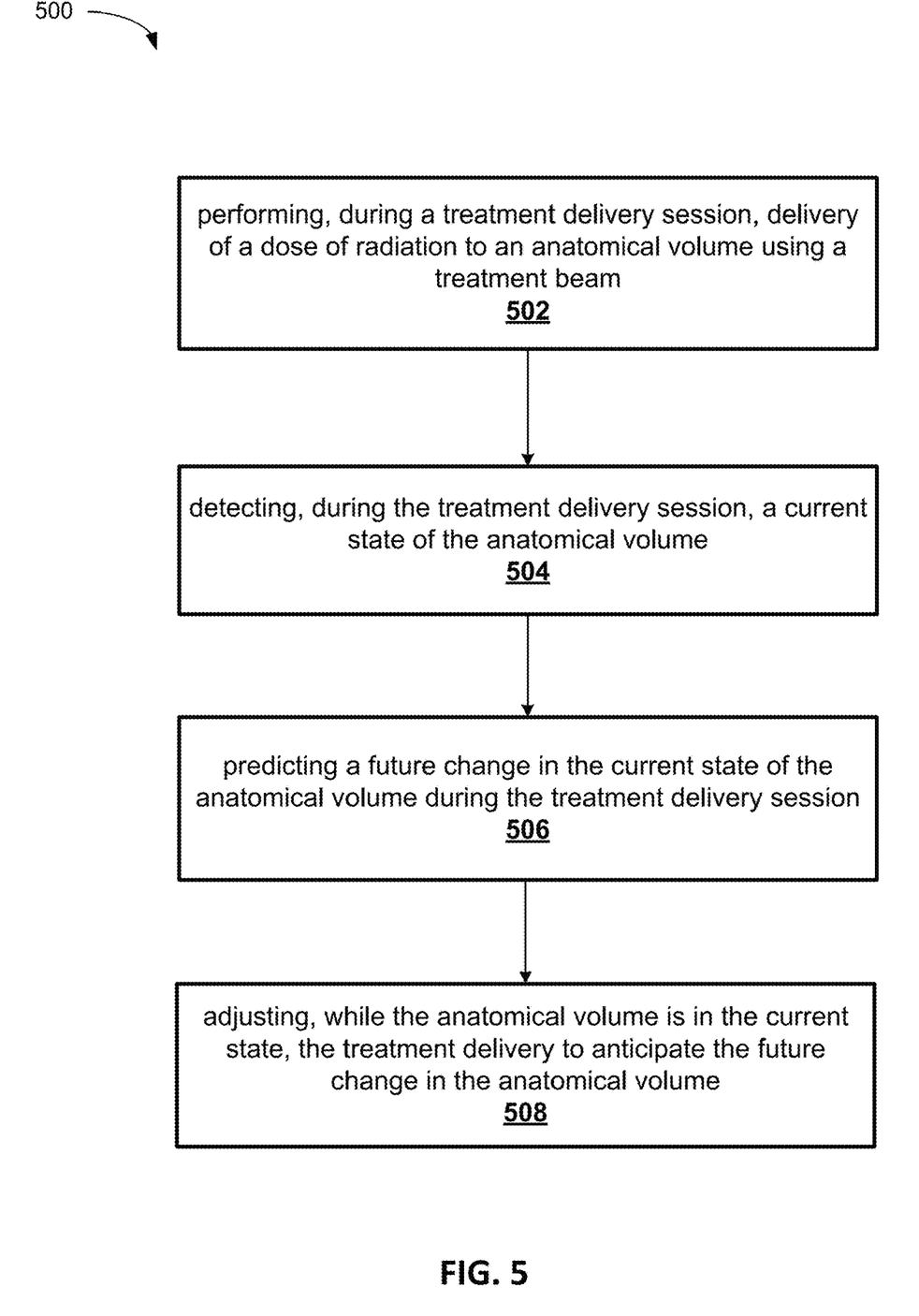
FIG. 5 is a flow diagram depicting a method performing prospective and retrospective on-line adaptive radiotherapy, according to some embodiments.

FIG. 5 is a flow diagram depicting a method performing prospective and retrospective on-line adaptive radiotherapy, according to some embodiments. Method 500 may be performed by processing logic that may comprise hardware (e.g., circuitry, dedicated logic, programmable logic, a processor, a processing device, a central processing unit (CPU), a system-on-chip (SoC), etc.), software (e.g., instructions and/or an application that is running/executing on a processing device), firmware (e.g., microcode), or a combination thereof. In some embodiments, method 500 may be performed by a prospective and retrospective on-line adaptive radiotherapy (PRO-ART) system, such as PRO-ART system 401 in FIG. 4. In some embodiments, the PRO-ART system 401 in FIG. 4 may perform one or more function blocks of method 500 by using a radiation treatment system, such as helical radiation delivery system 100 in FIG. 1, the radiation treatment system 200 in FIG. 2, or the C-arm gantry-based radiation treatment system 300 in FIG. 3.

With reference to FIG. 5, method 500 illustrates example functions used by various embodiments. Although specific function blocks ("blocks") are disclosed in method 500, such blocks are examples. That is, embodiments are well suited to performing various other blocks or variations of the blocks recited in method 500. It is appreciated that the blocks in method 500 may be performed in an order different than presented, and that not all of the blocks in method 500 may be performed.

As shown in FIG. 5, the method 500 includes the block 502 of performing, during a treatment delivery session, delivery of a dose of radiation to an anatomical volume. The method 500 includes the block 504 of detecting, during the treatment delivery session, a current state of the anatomical volume. The method 500 includes the block 506 of predicting a future change in the current state of the anatomical volume during the treatment delivery session. The method 500 includes the block 508 of adjusting, while the anatomical volume is in the current state, the treatment delivery to anticipate the future change in the anatomical volume.

In some embodiments, any of blocks 502-508 may be iteratively performed to interleave one or more treatment beams during a treatment session in order to get multiple passes at the anatomical volume. That is, the PRO-ART system 401 may determine the pass during treatment in which the patient configuration is closest to the planned patient configuration. In some embodiments, the interleaf spacing can be adjusted and/or optimized to improve the chances of getting good shots at the target.

Figure 6:
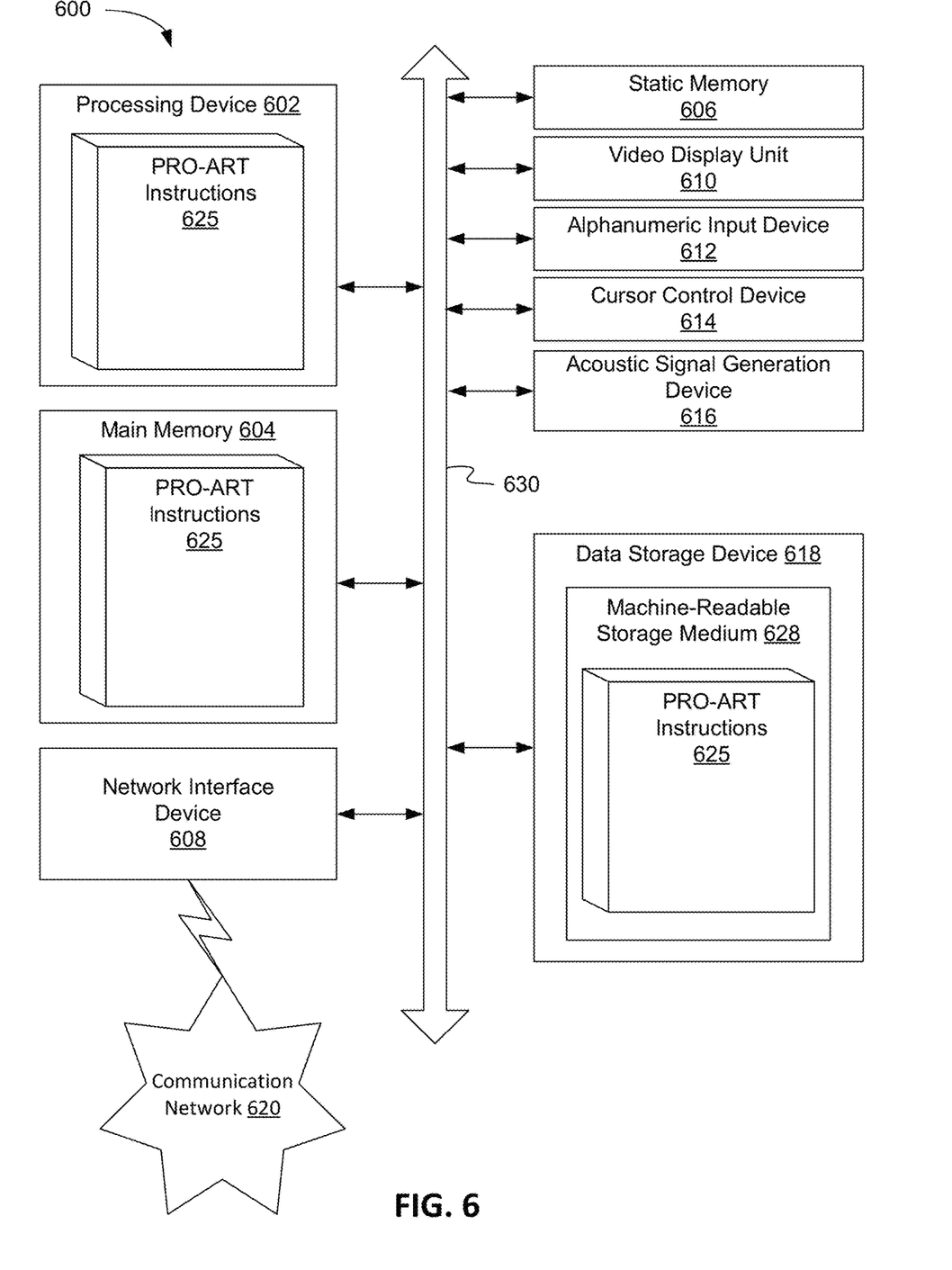
FIG. 6 is a block diagram of an example computing device 600 that may perform one or more of the operations described herein, in accordance with some embodiments.

FIG. 6 is a block diagram of an example computing device 600 that may perform one or more of the operations described herein, in accordance with some embodiments. Computing device 600 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 600 may include a processing device (e.g., a general purpose processor, a PLD, etc.) 602, a main memory 604 (e.g., synchronous dynamic random access memory (DRAM), read-only memory (ROM)), a static memory 606 (e.g., flash memory and a data storage device 618), which may communicate with each other via a bus 630.

Processing device 602 may be provided by one or more general-purpose processing devices such as a microprocessor, central processing unit, or the like. In an illustrative example, processing device 602 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 602 may also comprise one or more special-purpose processing devices such as an application specific integrated circuit (ASIC), a field programmable gate array (FPGA), a digital signal processor (DSP), network processor, or the like. The processing device 602 may be configured to execute the operations described herein, in accordance with one or more aspects of the present disclosure, for performing the operations and steps discussed herein.

Computing device 600 may further include a network interface device 608 which may communicate with a communication network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 616 (e.g., a speaker). In one embodiment, video display unit 610, alphanumeric input device 612, and cursor control device 614 may be combined into a single component or device (e.g., an LCD touch screen).

Data storage device 618 may include a computer-readable storage medium 628 on which may be stored one or more sets of instructions that may include prospective and retrospective on-line adaptive radiotherapy (PRO-ART) 625 for carrying out the operations of the PRO-ART system 401 in FIG. 4 as described herein, in accordance with one or more aspects of the present disclosure. The PRO-ART instructions 625 may also reside, completely or at least partially, within main memory 604 and/or within processing device 602 during execution thereof by computing device 600, main memory 604 and processing device 602 also constituting computer-readable media. The PRO-ART instructions 625 may further be transmitted or received over a communication network 620 via network interface device 608.

While computer-readable storage medium 628 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

Unless specifically stated otherwise, terms such as "performing," "detecting," "predicting," "adjusting," or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general purpose computing device selectively programmed by a computer program stored in the computing device. Such a computer program may be stored in a computer-readable non-transitory storage medium.

The methods and illustrative examples described herein are not inherently related to any particular computer or other apparatus. Various general purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. § 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the present disclosure to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the present disclosure is not to be limited to the details given herein, but may be modified within the scope and equivalents of the appended claims.

What is claimed is:

1. A method, comprising:
   performing, during a treatment delivery session, a delivery of a dose of radiation to an anatomical volume using a treatment beam;
   detecting, during the treatment delivery session, a current state of the anatomical volume based on an imaging scan;
   determining, based on a model of the anatomical volume, a future change in the current state of the anatomical volume during the treatment delivery session, wherein the model comprises at least one of anatomic structures, a motion model of the anatomical volume, or a deformation model of the anatomical volume; and
   adjusting, while the anatomical volume is in the current state, a treatment delivery to anticipate the future change in the current state of the anatomical volume during the treatment delivery session.

2. The method of claim 1, wherein performing, during the treatment delivery session, the delivery of the dose of radiation to the anatomical volume using the treatment beam is based on a treatment plan for a planned dose of radiation, and further comprising:
   determining that the future change in the current state of the anatomical volume during the treatment delivery session will cause a dose difference between the dose of radiation that is delivered to the anatomical volume and the planned dose of radiation.

3. The method of claim 1, further comprising:

determining that the future change in the current state of the anatomical volume during the treatment delivery session will cause one or more imaging times used for motion tracking of the anatomical volume to be aliased on a breathing phase; and capturing, while the anatomical volume is in the current state, an image at a different breathing phase.

4. The method of claim 1, wherein detecting the current state of the anatomical volume based on the imaging scan comprises:

detecting the current state of the anatomical volume based on one or more respiratory traces or one or more images.

5. The method of claim 4, wherein the one or more images comprise a computed tomography (CT) image or an X-ray image.

6. The method of claim 4, wherein the one or more images comprise a positron emission tomography (PET) image or a magnetic resonance imaging (MM) image.

7. The method of claim 1, wherein adjusting, while the anatomical volume is in the current state, the treatment delivery comprises at least one of adjusting the treatment beam or adjusting imaging parameters.

8. The method of claim 1, further comprising:

determining that the future change in the current state of the anatomical volume during the treatment delivery session is caused by a respiratory motion of the anatomical volume.

9. The method of claim 8, further comprising:

in response to determining that the future change in the current state of the anatomical volume during the treatment delivery session is caused by the respiratory motion of the anatomical volume:

adjusting the treatment beam to increase the dose of radiation to the anatomical volume while the anatomical volume is in the current state; and adjusting the treatment beam to decrease the dose of radiation to the anatomical volume while the anatomical volume is in a future configuration corresponding to the future change in the current state of the anatomical volume during the treatment delivery session.

10. The method of claim 1, further comprising:

predicting, while the anatomical volume is in the current state, that a future state of the anatomical volume will cause a degradation of an ability to track a motion of the anatomical volume; and adjusting, while the anatomical volume is in the current state, one or more imaging control parameters to mitigate the degradation of the ability to track the motion of the anatomic volume in the future state.

11. The method of claim 1, further comprising:

determining that the future change in the current state of the anatomical volume during the treatment delivery session is caused by a deformation that affects at least one of a relative position of a region of interest, wherein the deformation of the at least one of the relative position of the region of interest is unrelated to a respiratory motion of the anatomical volume.

12. The method of claim 11, further comprising:

in response to determining that the future change in the current state of the anatomical volume during the treatment delivery session is caused by the deformation:

adjusting the treatment beam to increase the dose of radiation to the anatomical volume when the treatment beam does not intersect critical structures; and adjusting the treatment beam to decrease the dose of radiation to the anatomical volume when the treatment beam intersects the critical structures.

13. The method of claim 1, wherein performing the delivery of the dose of radiation to the anatomical volume using the treatment beam comprises generating the treatment beam for a proton therapy.

14. The method of claim 1, wherein performing, during the treatment delivery session, the delivery of the dose of radiation to the anatomical volume using the treatment beam comprises generating the treatment beam, and further comprising:

determining that the future change in the current state of the anatomical volume during the treatment delivery session causes an absence of the anatomical volume from a field of view of the treatment beam during a movement through a plurality of treatment beam directions around the anatomical volume.

15. The method of claim 14, further comprising:

in response to determining that the future change in the current state of the anatomical volume during the treatment delivery session causes the absence of the anatomical volume from the field of view of the treatment beam during the movement through the plurality of treatment beam directions around the anatomical volume:

adjusting the treatment beam to prevent the dose of radiation to the anatomical volume during a successive motion through the plurality of treatment beam directions around the anatomical volume; and adjusting the treatment beam to increase the dose of radiation to the anatomical volume during different motions of the treatment beam around the anatomical volume, wherein the anatomical volume is continuously within the field of view of the treatment beam during the successive motion through the plurality of treatment beam directions.

16. The method of claim 14, further comprising:

determining a position of the anatomical volume during a successive movement through the plurality of treatment beam directions around the anatomical volume to generate a determined target position;

determining a confidence score associated with the determined target position; and determining the absence of the anatomical volume from the field of view of the treatment beam based on the confidence score.

17. The method of claim 14, wherein adjusting, while the anatomical volume is in the current state, the treatment delivery to anticipate the future change in the current state of the anatomical volume during the treatment delivery session comprises: adjusting one or more control parameters of a collimator.

18. A radiation delivery system, comprising:

a radiation source to generate a treatment beam for a delivery of a dose of radiation; and a processing device, operatively coupled to the radiation source, to:

perform, during a treatment delivery session, the delivery of the dose of radiation to an anatomical volume;

detect, during the treatment delivery session, a current state of the anatomical volume;

determine, based on a model of the anatomical volume, a future change in the current state of the anatomical volume during the treatment delivery session, wherein the model comprises at least one of anatomic structures, a motion model of the anatomical volume, or a deformation model of the anatomical volume; and adjust, while the anatomical volume is in the current state, a treatment delivery to anticipate the future change in the current state of the anatomical volume during the treatment delivery session.

19. The radiation delivery system of claim 18, wherein the processing device performs, during the treatment delivery session, the delivery of the dose of radiation to the anatomical volume based on a treatment plan for a planned dose of radiation, and wherein the processing device further to:

determine that the future change in the current state of the anatomical volume during the treatment delivery session will cause a dose difference between the dose of radiation that is delivered to the anatomical volume and the planned dose of radiation.

20. The radiation delivery system of claim 18, wherein the processing device further to:

determine that the future change in the current state of the anatomical volume during the treatment delivery session will cause one or more imaging times used for motion tracking of the anatomical volume to be aliased on a breathing phase; and capture, while the anatomical volume is in the current state, an image at a different breathing phase.

21. The radiation delivery system of claim 18, wherein the processing device further to:

detect the current state of the anatomical volume based on one or more respiratory traces or one or more images.

22. The radiation delivery system of claim 21, wherein the one or more images comprise a computed tomography (CT) image or an X-ray image.

23. The radiation delivery system of claim 21, wherein the one or more images comprise a positron emission tomography (PET) image or a magnetic resonance imaging (MRI) image.

24. The radiation delivery system of claim 18, wherein the processing device further to:

adjust the treatment beam, or adjust imaging parameters.

25. The radiation delivery system of claim 18, wherein the processing device further to:

determine that the future change in the current state of the anatomical volume during the treatment delivery session is caused by a respiratory motion of the anatomical volume.

26. The radiation delivery system of claim 18, wherein the processing device further to:

adjust the treatment beam to increase the dose of radiation to the anatomical volume while the anatomical volume is in the current state; and adjust the treatment beam to decrease the dose of radiation to the anatomical volume while the anatomical volume is in a future configuration corresponding to the future change in the current state of the anatomical volume during the treatment delivery session.

27. The radiation delivery system of claim 18, wherein the processing device further to:

predict, while the anatomical volume is in the current state, that a future state of the anatomical volume will cause a degradation of an ability to track a motion of the anatomical volume; and adjust, while the anatomical volume is in the current state, one or more imaging control parameters to mitigate the degradation of the ability to track the motion of the anatomical volume in the future state.

28. A non-transitory computer-readable storage medium including instructions which, when executed by a processing device of a radiation delivery system, cause the radiation delivery system to:

perform, during a treatment delivery session, a delivery of a dose of radiation to an anatomical volume;

detect, during the treatment delivery session, a current state of the anatomical volume;

determine, based on a model of the anatomical volume, a future change in the current state of the anatomical volume during the treatment delivery session, wherein the model comprises at least one of anatomic structures, a motion model of the anatomical volume, or a deformation model of the anatomical volume; and adjust, while the anatomical volume is in the current state, a treatment delivery to anticipate the future change in the current state of the anatomical volume during the treatment delivery session.

\* \* \* \* \*